United States Patent
Eisert et al.

(10) Patent No.: US 12,152,219 B2
(45) Date of Patent: Nov. 26, 2024

(54) LIQUID CLEANING AGENT CONCENTRATE COMPRISING A FATTY ALCOHOL-BASED EO/PO COPOLYMER AND A C10-C18 AMINO ACID-BASED SURFACTANT MIXTURE

(71) Applicant: CHEMISCHE FABRIK DR. WEIGERT GMBH & CO. KG, Hamburg (DE)

(72) Inventors: Dennis Eisert, Börnsen (DE); Bastian Wulff, Hamburg (DE); Matthias Springer, Hamburg (DE)

(73) Assignee: CHEMISCHE FABRIK DR. WEIGERT GMBH & CO. KG, Hamburg (DE)

( * ) Notice: Subject to any disclaimer, the term of this patent is extended or adjusted under 35 U.S.C. 154(b) by 0 days.

(21) Appl. No.: 18/250,141

(22) PCT Filed: Oct. 22, 2021

(86) PCT No.: PCT/EP2021/079352
§ 371 (c)(1),
(2) Date: Apr. 21, 2023

(87) PCT Pub. No.: WO2022/084512
PCT Pub. Date: Apr. 28, 2022

(65) Prior Publication Data
US 2023/0399593 A1 Dec. 14, 2023

(30) Foreign Application Priority Data
Oct. 23, 2020 (EP) ..................................... 20203505

(51) Int. Cl.
| | |
|---|---|
| C11D 1/83 | (2006.01) |
| A61L 2/00 | (2006.01) |
| C11D 1/10 | (2006.01) |
| C11D 1/72 | (2006.01) |
| C11D 3/00 | (2006.01) |
| C11D 3/48 | (2006.01) |

(52) U.S. Cl.
CPC .............. *C11D 1/72* (2013.01); *A61L 2/0088* (2013.01); *C11D 1/10* (2013.01); *C11D 1/83* (2013.01); *C11D 3/0047* (2013.01); *C11D 3/48* (2013.01); *C11D 2111/14* (2024.01)

(58) Field of Classification Search
CPC .... C11D 1/83; C11D 1/10; C11D 1/22; C11D 1/72; C11D 1/722; C11D 3/30; C11D 3/38618; C11D 2111/14; C11D 2111/16
See application file for complete search history.

(56) References Cited

U.S. PATENT DOCUMENTS

| | | | | |
|---|---|---|---|---|
| 5,756,080 | A * | 5/1998 | Janchitraponvej | A61K 8/84 424/70.122 |
| 5,767,055 | A * | 6/1998 | Choy | C11D 3/3956 510/480 |
| 5,837,670 | A * | 11/1998 | Hartshorn | C11D 3/3945 510/501 |
| 6,281,178 | B1 | 8/2001 | Ryklin et al. | |
| 6,627,586 | B1 * | 9/2003 | Brooks | C11D 1/94 510/159 |
| 2005/0029296 | A1 * | 2/2005 | Hansen | D06L 1/04 222/145.5 |
| 2008/0095733 | A1 * | 4/2008 | Griffin | C11D 1/83 510/130 |
| 2010/0261631 | A1 | 10/2010 | Isobe et al. | |
| 2011/0301069 | A1 * | 12/2011 | Dooley | C11D 1/83 510/161 |
| 2013/0067663 | A1 * | 3/2013 | Hufnagel | C11D 3/3907 510/310 |
| 2013/0333730 | A1 * | 12/2013 | Dooley | C11D 3/3463 510/161 |
| 2014/0238445 | A1 * | 8/2014 | Stokes | C11D 3/48 134/28 |
| 2016/0230126 | A1 * | 8/2016 | Strodtholz | B08B 3/10 |
| 2018/0201879 | A1 | 7/2018 | Gonzales et al. | |
| 2019/0169546 | A1 * | 6/2019 | Andersen | C11D 3/386 |

FOREIGN PATENT DOCUMENTS

| | | |
|---|---|---|
| CN | 106635488 A | 5/2017 |
| EP | 1327674 A1 | 7/2003 |
| JP | 2012140483 A | 7/2012 |
| JP | 2015017151 A | 1/2015 |
| WO | WO 95/33027 A1 | 12/1995 |
| WO | WO 95/33043 A1 | 12/1995 |
| WO | WO 1995/033030 A1 | 12/1995 |
| WO | WO 02/02727 A1 | 1/2002 |
| WO | WO 2012/038755 A1 | 3/2012 |
| WO | WO 2015/168658 A1 | 11/2015 |
| WO | WO 2016/007291 A1 | 1/2016 |
| WO | WO 2018/113979 A1 | 6/2018 |

OTHER PUBLICATIONS

English translation of International Search Report, PCT/EP2021/079352, mailed Dec. 22, 2021, 2 pages.

* cited by examiner

*Primary Examiner* — Charles I Boyer
(74) *Attorney, Agent, or Firm* — Anne M. Reynolds; Casimir Jones, S.C.

(57) ABSTRACT

Liquid cleaning agent concentrate comprising: a. at least one fatty alcohol alkoxylate, b: at least one amino acid-based surfactant, c. at least one hydrotropic agent, and d. at least one enzyme, preferably proteolytic enzyme, a pH of the liquid cleaning agent concentrate being 9 or >9. The invention also relates to a ready-to-use solution; to uses thereof for cleaning and/or disinfecting objects and to cleaning methods.

18 Claims, 6 Drawing Sheets

Figure 1:
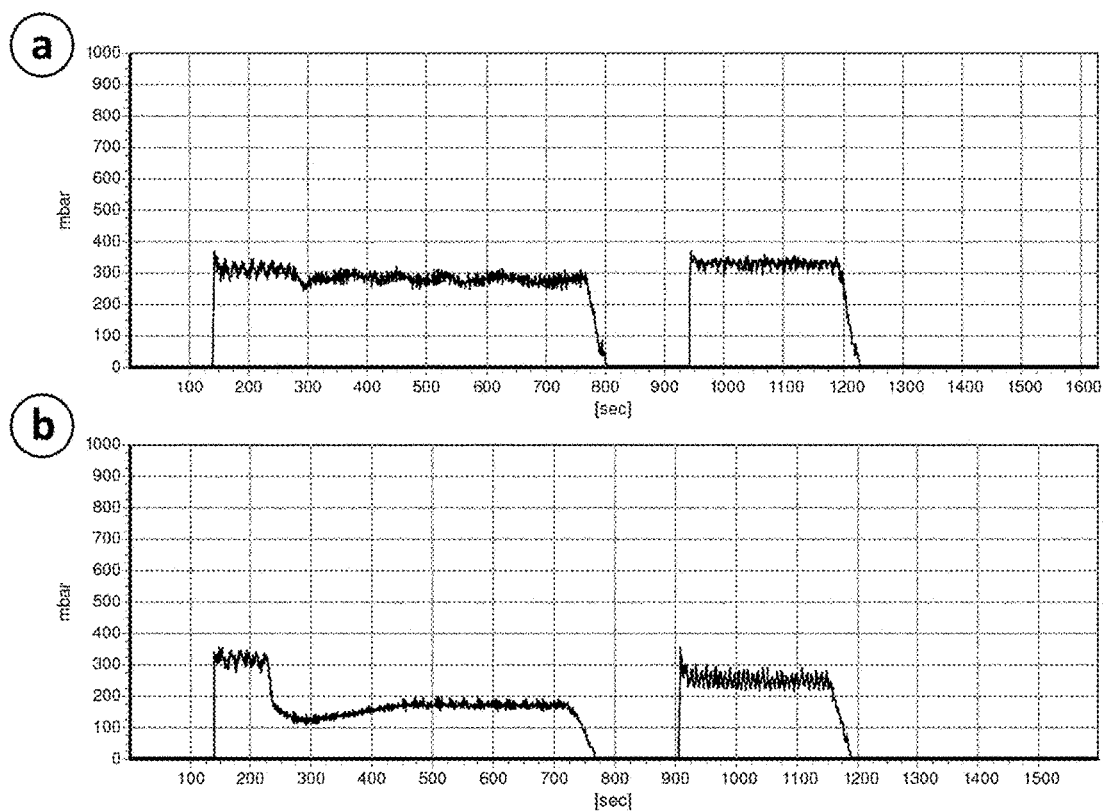

LIQUID CLEANING AGENT CONCENTRATE COMPRISING A FATTY ALCOHOL-BASED EO/PO COPOLYMER AND A C10-C18 AMINO ACID-BASED SURFACTANT MIXTURE

The present invention relates to a liquid cleaning agent concentrate, ready-to-use application solutions, uses thereof for cleaning and/or disinfecting objects and cleaning methods.

Medical and surgical instruments and apparatus are usually cleaned by machine in hospitals using alkaline cleaning agents and then chemically or thermally disinfected. Strongly alkaline cleaning agents can have an aggressive effect on sensitive surfaces. Mildly alkaline enzymatic cleaning agents are therefore preferred, but they have the disadvantages of unsatisfactory cleaning performance and high application concentrations.

Moreover, cleaning agents which contain anionic surfactants and are known in the prior art have a tendency toward strong foam formation, which is disadvantageous for applicability in machine cleaning processes. Pronounced foam formation leads to a drop in the metering pump pressure and thus ultimately to the entire cleaning process being aborted. Therefore, in the prior art, anionic surfactants are selected from the viewpoint of low foam formation and the disadvantages thereof as regards cleaning performance are accepted.

The invention is based on the object of providing a liquid cleaning agent concentrate and a ready-to-use application solution thereof which enable very good cleaning performance at only a low application concentration and at the same time exhibit ideal foaming behavior and high material compatibility on various materials.

The invention achieves these objects by the features of the claims. Claim 1 includes a liquid cleaning agent concentrate for machine cleaning and/or disinfection of medical and/or surgical instruments and/or instruments and/or apparatus, comprising:
 a. at least one fatty alcohol alkoxylate,
 b. at least one amino acid-based surfactant,
 c. at least one hydrotrope, and
 d. at least one enzyme, preferably proteolytic enzyme,
wherein the pH of the liquid cleaning agent concentrate is 9 or >9.

Preferred embodiments can be found in the dependent claims.

In the context of the invention, the liquid cleaning agent concentrate according to the invention may be diluted with water or a water-containing solvent mixture to give the ready-to-use application solution. However, this does not preclude the possibility that the liquid cleaning agent concentrate itself may contain water or a water-based solvent mixture.

The liquid cleaning agent concentrate preferably has a pH of 9-12, more preferably 10-12, even more preferably 10-11.

1. Fatty Alcohol Alkoxylates

The liquid cleaning agent concentrate comprises at least one fatty alcohol alkoxylate. The at least one fatty alcohol alkoxylate is preferably selected from fatty alcohol ethoxylates (FAEO) and fatty alcohol propoxylates (FAPO), butyl-etherified fatty alcohol ethoxylates (FAEOBV), butyl-etherified fatty alcohol propoxylates (FAPOBV), methyl-etherified fatty alcohol ethoxylates (FAEOMV), methyl-etherified fatty alcohol propoxylates (FAPOMV), fatty alcohol-based EO/PO copolymers (FAEOPO), methyl-etherified fatty alcohol-based EO/PO copolymers (FAEOPOMV) and butyl-etherified fatty alcohol-based EO/PO copolymers (FAEOPOBV). The fatty alcohol alkoxylate is more preferably a fatty alcohol-based EO/PO copolymer.

The at least one fatty alcohol alkoxylate may comprise 0-10 EO units, preferably 1-4 EO units, more preferably 1-2 EO units. Furthermore, the at least one fatty alcohol alkoxylate may comprise 0-8 PO units, preferably 1-8 PO units, more preferably 4-8 PO units.

The fatty alcohol alkoxylate may have at least one C6-C16 fatty alcohol radical, more preferably C12-C15 fatty alcohol radical.

The fatty alcohol alkoxylate is preferably selected from the group consisting of C12-C15 fatty alcohol radical having 2 EO/6 PO units, C12-C15 fatty alcohol radical having 8 EO/4 PO units, butyl- or methyl-etherified C12-C14 fatty alcohol radical having 10 EO units, C10-C12 fatty alcohol radical having 6 EO/8 PO units, C12-C14 fatty alcohol radical having 2 EO/4 PO units, C12-C14 fatty alcohol radical having 4 EO/5 PO units, C13-C15 fatty alcohol radical having 5 EO/3 PO units and methyl-etherified C13-C15 fatty alcohol radical having 5 EO/3 PO units, and the fatty alcohol alkoxylate is more preferably selected from C12-C15 fatty alcohol radical having 2 EO/6 PO units, C12-C14 fatty alcohol radical having 2 EO/4 PO units and C12-C14 fatty alcohol radical having 4 EO/5 PO units.

The fatty alcohol alkoxylate in the liquid cleaning concentrate is preferably present at a proportion by weight of 0.1 to 9% by weight, more preferably from 0.4 to 2% by weight, based on the total mass of the liquid cleaning agent concentrate.

2. Amino Acid-Based Surfactants

The liquid cleaning agent concentrate comprises at least one amino acid-based surfactant. The amino acid-based surfactant is preferably selected from compounds having a saturated or monounsaturated C10-C18 carbon radical, preferably a saturated C12-C16 carbon radical.

The amino acid-based surfactant is preferably selected from sarcosines, taurines, glutamic acids and salts thereof. The salts can be alkali metal salts, preferably sodium and potassium salts. The amino acid-based surfactant is more preferably a sarcosine and the sodium salt thereof.

Preferred embodiments of the amino acid-based surfactant are selected from lauroyl sarcosine, oleoyl sarcosine, myristoyl sarcosine, stearoyl sarcosine and lauroyl glutamic acid and sodium salts thereof. Particular preference is given to lauroyl sarcosine and lauroyl glutamic acid and sodium salts thereof.

The amino acid-based surfactant in the liquid cleaning agent concentrate is preferably present at a proportion by weight of 0.05 to 5% by weight, more preferably 0.08 to 2% by weight, even more preferably from 0.1 to 2% by weight, based on the total mass of the liquid cleaning agent concentrate.

3. Hydrotropes

The liquid cleaning agent concentrate comprises at least one hydrotrope. In the context of the invention, "hydrotropes" are compounds that act as solubilizers. According to the invention, these are in particular amphiphilic compounds having a relatively small polar moiety and a larger non-polar moiety, which are soluble in both non-polar and polar solvents. Compared to surfactants, hydrotropes exhibit less hydrophobic properties and higher solubility in water. The polar moiety ensures higher solubility in water while the non-polar moiety acts as a functional group. Hydrotropes according to the invention make it possible in particular to formulate a clear and stable liquid cleaning agent concentrate and a clear ready-to-use application solution. According to the invention, the compounds defined as amino acid-based surfactants and/or fatty alcohol alkoxylates are preferably not hydrotropes.

The at least one hydrotrope is selected from:
- alkyl sulfates, preferably C6-C10-alkyl sulfates and sodium salts thereof, more preferably sodium octyl sulfate and sodium ethylhexyl sulfate;
- alkyl sulfonates, preferably C6-C10-alkyl sulfonates;
- aromatic sulfonates, preferably xylene sulfonate, p-toluenesulfonate and sodium salts thereof;
- propionates, preferably isooctylimino dipropionate, n-octylimino dipropionate, caprylic and capric amphopropionate;
- C4-C10 ether carboxylic acids having 4-10 EO units, preferably alkyl(8) polyether carboxylic acid having 8 EO units and alkyl(4-8) polyether carboxylic acid having 5 EO units;
- alkyl glycosides, alkyl diglycosides, alkyl polyglycosides and mixtures thereof, wherein the alkyl radical is preferably a branched or unbranched C4-C16-alkyl radical and the glycoside radical is preferably selected from hexose unit and pentose unit, more preferably selected from glucopyranose unit and xylopyranose unit.

Particularly preferred as the hydrotrope are sodium octyl sulfate, sodium ethylhexyl sulfate or a mixture thereof.

The hydrotrope in the liquid cleaning agent concentrate is preferably present at a proportion by weight of 0.05 to 13% by weight, more preferably from 0.1 to 7% by weight, even more preferably 0.15 to 3.5% by weight, based on the total mass of the liquid cleaning agent concentrate.

4. Enzyme

The enzyme is preferably a proteolytic enzyme or enzyme mixture.

The enzyme or the enzyme mixture in the liquid cleaning agent concentrate is preferably present at a proportion by weight of 0.05 to 4% by weight, more preferably from 0.1 to 2% by weight, based on the total mass of the liquid cleaning agent concentrate. The enzyme activity is preferably $30\times10^{-2}$ to $100\times10^{-2}$ KNPU/g, more preferably $70\times10^{-2}$ to $85\times10^{-2}$ KNPU/g.

5. Further Constituents

The liquid cleaning agent concentrate may also comprise further constituents selected from alkanolamines, alkali metal hydroxides, chelating agents, solvents, corrosion inhibitors, fragrances and dyes.

The alkanolamine is preferably selected from monoethanolamine, triethanolamine, monoisopropanolamine and mixtures thereof. The alkanolamine or mixture thereof can serve in particular to adjust the alkalinity of the liquid cleaning agent concentrate. Monoethanolamine has the advantage of being a good protein purifier. The alkanolamine or mixture thereof in the liquid cleaning agent concentrate is preferably present at a proportion by weight of 1 to 26% by weight, more preferably from 4 to 18% by weight, based on the total mass of the liquid cleaning agent concentrate.

The alkali metal hydroxide is preferably sodium hydroxide and/or potassium hydroxide, more preferably potassium hydroxide. In the context of the invention, the alkali metal hydroxide serves in particular to adjust the alkalinity of the liquid cleaning agent concentrate. Potassium hydroxide in the liquid cleaning agent concentrate is preferably present at a proportion by weight of 1 to 8% by weight, more preferably 2 to 5% by weight, based on the total mass of the liquid cleaning agent concentrate. It has been found that there is no significant increase in damage to anodized aluminum despite this high proportion by weight of potassium hydroxide of 2 to 5% by weight.

The chelating agent may be selected from the group consisting of phosphonates, preferably from salts of phosphonobutanetricarboxylic acid (PBTC), of aminotrismethylenephosphonic acid (ATMP), of 1-hydroxyethane-1,1-diphosphonic acid (HEDP), of diethylenetriamine penta (methylenephosphonic acid) (DTPMP) and mixtures thereof, more preferably from the sodium salts of phosphonobutanetricarboxylic acid, of aminotrismethylenephosphonic acid and mixtures thereof; aminopolycarboxylic acids, preferably from hydroxyethylethylenediaminetriacetic acid (HEDTA), ethylenediaminetetraacetic acid (EDTA), glutamic acid N,N-diacetic acid (GLDA), iminodisuccinic acid (IDS), methylglycine diacetic acid (MGDA), ethylenediaminedisuccinic acid (EDDS), polyaspartic acids, nitrilotriacetic acid (NTA), nitrilomonoacetic dipropionic acid, nitrilotripropionic acid, β-alanine diacetic acid (β-ADA), diethylenetriaminepentaacetic acid, 1,3-propylenediaminetetraacetic acid, 1,2-propylenediaminetetraacetic acid, N-(alkyl)ethylenediaminetriacetic acid, ethylenediaminetriacetic acid, cyclohexylene-1,2-diaminetetraacetic acid, serine diacetic acid, isoserine diacetic acid, L-aspartic acid diacetic acid, salts thereof and mixtures thereof, more preferably from the sodium salts of HEDTA, of MGDA and mixtures thereof; and hydroxycarboxylic acids, hydroxypolycarboxylic acids and salts thereof, preferably gluconic acid, glucoheptanoic acid, malic acid, tartaric acid, mucic acid, lactic acid, glutaric acid, citric acid, tartronic acid, lactobionic acid and sucrose mono-, di- and tricarboxylic acid and salts thereof, more preferably from the sodium salt of glucoheptonic acid. The chelating agent is more preferably a mixture of at least one phosphonate and at least one aminopolycarboxylic acid, hydroxycarboxylic acid or salt thereof. The chelating agent mixture may also comprise a further aminopolycarboxylic acid which is likewise selected from the above-defined aminopolycarboxylic acids and salts thereof, wherein the first and the second aminopolycarboxylic acid are mutually different. The phosphonate or the phosphonate mixture in the liquid cleaning agent concentrate can be present at a proportion by weight of 1 to 13% by weight, preferably from 2 to 10% by weight, more preferably 3 to 8% by weight, based on the total mass of the liquid cleaning agent concentrate. The aminopolycarboxylic acids, the hydroxycarboxylic acids, the hydroxypolycarboxylic acid, salts thereof or mixtures thereof in the liquid cleaning agent concentrate can be present at a proportion by weight of 1 to 10% by weight, preferably from 2 to 8% by weight, more preferably from 3 to 6% by weight, based on the total mass of the liquid cleaning agent concentrate.

The solvent can be water or a water-containing solvent mixture. Preference is given to solvent mixtures which, in addition to water, comprise organic solvents selected from ethanol, 2-propanol, glycols, glycerol and mixtures thereof. A preferred glycol is 1,2-propylene glycol. The organic solvent in the liquid cleaning agent concentrate is preferably present at a proportion by weight of 0.5 to 10% by weight, more preferably from 3 to 7% by weight, based on the total mass of the liquid cleaning agent concentrate.

Water in the liquid cleaning agent concentrate is preferably present at a proportion by weight of 30 to 90% by weight, more preferably from 35 to 70% by weight, even more preferably from 35 to 60% by weight, still more preferably 35 to 50% by weight, even further preferably 35 to 45% by weight, based on the total mass of the liquid cleaning agent concentrate.

The liquid cleaning agent concentrate can moreover contain phosphoric acid, which preferably serves as corrosion inhibitor. Phosphoric acid in the liquid cleaning agent concentrate is preferably present at a proportion by weight of 0.1 to 20% by weight, more preferably 0.2 to 7% by weight, even more preferably 0.3 to 5% by weight, based on the total mass of the liquid cleaning agent concentrate.

An upper limit for a total proportion by weight of fatty alcohol alkoxylate, amino acid-based surfactant and hydrotrope in the liquid cleaning agent concentrate is preferably 30% by weight, more preferably 20% by weight, even more preferably 13% by weight, still more preferably 10% by weight, even further preferably 8% by weight, still further preferably 5% by weight, based on the total mass of the liquid detergent concentrate.

Surfactants (i.e. cationic, anionic, zwitterionic, non-ionic surfactants) in the liquid cleaning agent concentrate are preferably present at most at a proportion by weight of up to 30% by weight, more preferably up to 20% by weight, even more preferably up to 18% by weight, still more preferably up to 13% by weight, even further preferably up to 9% by weight, still further preferably up to 7.5% by weight, based on the total mass of the liquid cleaning agent concentrate.

Anionic surfactants in the liquid cleaning agent concentrate are preferably present at most at a proportion by weight of up to 20% by weight, more preferably up to 18% by weight, even more preferably up to 13% by weight, still more preferably up to 8% by weight, even further preferably up to 5% by weight, still further preferably up to 3% by weight, based on the total mass of the liquid cleaning agent concentrate. The invention is based on the surprising finding that the combination of fatty alcohol alkoxylate, amino acid-based surfactant and hydrotrope in the liquid cleaning agent concentrate has the following technical effects/advantages. The concentrate, containing precisely these three constituents, is a low-foaming cleaning formulation that achieves very good cleaning performance at only a low application concentration and at the same time exhibits high material compatibility when used on different materials.

The active ingredients present in the liquid cleaning agent concentrate according to the invention can be used at a significantly lower dosage than in the case of other cleaning agents known in the prior art. This is due in particular to a synergistic effect with respect to the cleaning performance. The cleaning performance achieved by the liquid cleaning agent concentrate containing the combination of fatty alcohol alkoxylate, amino acid-based surfactant and hydrotrope is significantly better than that of the respective individual components.

Anionic surfactants and also amino acid-based surfactants are generally strong foaming agents and are often used in a specific manner in the prior art in order to enhance this property in cleaning formulations. However, in the context of the invention, what is precisely not desired is strong foaming. Low-foaming constituents are required for application in machine cleaning processes, for example by means of an instrument washer or by means of washer disinfectors. This is because pronounced foam formation in the case of machine cleaning leads to a drop in the metering pump pressure and thus ultimately to the cleaning process being aborted. Surprisingly, foam formation is suppressed by the combination of fatty alcohol alkoxylate, amino acid-based surfactant and hydrotrope. In particular, the foam-forming effect of the amino acid-based surfactant is dampened by the addition of the fatty alcohol alkoxylate, and so it is possible to set a desired foaming behavior of the liquid cleaning agent concentrate.

In the prior art, the dispensing of surfactant-containing, enzymatic and mildly alkaline liquid cleaning agents in machine cleaning is usually done at a water temperature of about 40° C. This is necessary because the cleaning agents tend to foam excessively at lower temperatures. The disadvantage of this, however, is that the running time of the cleaning programs is longer, since the heating time from the inlet temperature (usually ca. 18-22° C.) up to 40° C. causes an initial delay before the cleaning agent can take effect. The liquid cleaning agent concentrate according to the invention, in contrast, makes it possible to carry out cold dispensing directly after the water inlet, at a temperature of preferably 38° C. or less, more preferably from 18 to 35° C., even more preferably from 20 to 30° C., still more preferably from 22 to 27° C., even further preferably at about 25° C., without the program being aborted due to excessive foam development. Such cold dispensing is currently not possible with the commercially available liquid cleaning agents known from the prior art. The cold dispensing of the liquid cleaning agent concentrate has independent inventive content.

Another important requirement for liquid cleaning agents is the highest possible material compatibility when used on different materials. The corrosion protection of stainless steel and (color) anodized aluminum parts is important, especially with regard to medical and/or surgical instruments and/or apparatus. Surprisingly, the liquid cleaning agent concentrate according to the invention has a high level of material compatibility. Especially the presence of the amino acid-based surfactant results in significantly improved corrosion inhibition characteristics on stainless steel and (color) anodized aluminum parts. In addition, surprisingly, improved shine and an improved feel, especially of stainless steel parts, are observed with more frequent use of the liquid cleaning agent concentrate according to the invention.

In the context of the invention, the hydrotrope also acts as a solubilizer for the fatty alcohol alkoxylate and to clarify the formulation within a certain temperature range. The test parameters that can be used for this purpose are the cloud point of the liquid cleaning formulations and the metering pump pressure during a machine washing operation. Surprisingly, the combination of constituents that is according to the invention achieves a cloud point of >40° C. This is particularly advantageous because this is generally also the application temperature or the storage temperature in the washer disinfector. By contrast, the cloud point without the combination according to the invention would only be around 20° C.

The invention further provides a ready-to-use application solution comprising 0.05 to 99.9% of the liquid cleaning agent concentrate according to the invention, wherein the pH of the ready-to-use application solution is 9 or >9, preferably 9-12, more preferably 10-12, even more preferably 10-11.

The ready-to-use application solution preferably comprises 0.05 to 10%, more preferably 0.1 to 1%, of the liquid cleaning agent concentrate according to the invention.

The constituents, properties and advantageous effects of the ready-to-use application solution listed above correspond to those previously defined for the liquid cleaning agent concentrate. However, the constituents in the ready-to-use application solution are present in the following proportions by weight:

The fatty alcohol alkoxylate in the ready-to-use application solution is preferably present at a proportion by weight of 0.00005 to 0.9% by weight, more preferably 0.0004 to 0.02% by weight, based on the total mass of the ready-to-use application solution.

The amino acid-based surfactant in the ready-to-use application solution is preferably present at a proportion by weight of 0.000025 to 0.5% by weight, more preferably 0.0001 to 0.02% by weight, based on the total mass of the ready-to-use application solution.

The hydrotrope in the ready-to-use application solution is preferably present at a proportion by weight of 0.000025 to 1.3% by weight, more preferably from 0.0001 to 0.07% by weight, even more preferably from 0.00015 to 0.035% by weight, based on the total mass of the ready-to-use application solution.

The enzyme or the enzyme mixture in the ready-to-use application solution is preferably present at a proportion by weight of 0.000025 to 0.4% by weight, more preferably from 0.0001 to 0.02% by weight, based on the total mass of the ready-to-use application solution.

The alkanolamine or mixture thereof in the ready-to-use application solution can be present at a proportion by weight of 0.0005 to 2.6% by weight, preferably from 0.004 to 0.18% by weight, based on the total mass of the ready-to-use application solution.

The chelating agent or the chelating agent mixture in the ready-to-use application solution can be present at a proportion by weight of 0.001 to 2.3% by weight, preferably 0.004 to 0.18% by weight, more preferably 0.006 to 0.14% by weight, based on the total mass of the ready-to-use application solution.

The organic solvent in the ready-to-use application solution can be present at a proportion by weight of 0.00025 to 1.0% by weight, preferably 0.003 to 0.07% by weight, based on the total mass of the ready-to-use application solution.

Water in the ready-to-use application solution can be present at a proportion by weight of 90.0 to 99.985% by weight, preferably 95.0 to 99.98% by weight, more preferably 99.6 to 99.96% by weight, based on the total mass of the ready-to-use application solution.

Phosphoric acid in the ready-to-use application solution can be present at a proportion by weight of 0.00005 to 2.5% by weight, more preferably 0.0002 to 0.14% by weight, even more preferably 0.0003 to 0.07% by weight, based on the total mass of the ready-to-use application solution.

An upper limit for a total proportion by weight of fatty alcohol alkoxylate, amino acid-based surfactant and hydrotrope in the ready-to-use application solution is preferably 2.7% by weight, more preferably 1% by weight, even more preferably 0.4% by weight, still more preferably 0.1% by weight, even further preferably 0.075% by weight, based on the total mass of the ready-to-use application solution.

Surfactants (i.e. cationic, anionic, zwitterionic, non-ionic surfactants) in the ready-to-use application solution are preferably present at most at a proportion by weight of up to 3% by weight, more preferably up to 2.7% by weight, even more preferably up to 1.5% by weight, still more preferably up to 1% by weight, even further preferably up to 0.075% by weight, based on the total mass of the ready-to-use application solution.

Anionic surfactants in the ready-to-use application solution are preferably present at most at a proportion by weight of up to 2.8% by weight, more preferably up to 2% by weight, even more preferably up to 1.8% by weight, still more preferably up to 1% by weight, even further preferably up to 0.5% by weight, still further preferably up to 0.1% by weight, yet further preferably up to 0.055% by weight, based on the total mass of the ready-to-use application solution.

The invention further provides for the use of the liquid cleaning agent concentrate according to the invention or the ready-to-use application solution according to the invention for cleaning and/or disinfection of objects, preferably for machine cleaning and/or disinfection of objects. In an advantageous embodiment, the liquid cleaning agent concentrate or the ready-to-use application solution are preferably dispensed cold, more preferably at a temperature of 38° C. or less, even more preferably from 18 to 35° C., still more preferably from 20 to 30° C., even further preferably from 22 to 27° C., still further preferably at about 25° C.

In the context of the present invention, machine cleaning is carried out without human intervention during an automatic program run, preferably in an instrument washer or in a washer disinfector. According to the invention, the wording "cleaning and/or disinfection" expresses the fact that the liquid cleaning agent concentrate and the ready-to-use application solution can be used both in the combination of cleaning and disinfection in a single method step and in program sequences in which a cleaning step is followed by a separate disinfection step. The objects are preferably medical and/or surgical instruments and/or apparatus.

The invention further provides the method for cleaning medical and/or surgical instruments and/or apparatus, characterized by the following steps:
 a) preparing a ready-to-use application solution as claimed in the dependent claims,
 b) cleaning the medical and/or surgical instruments and/or apparatus with the ready-to-use application solution.

In an advantageous embodiment, the ready-to-use application solution is preferably prepared cold, more preferably at a temperature of 38° C. or less, even more preferably from 18 to 35° C., still more preferably from 20 to 30° C., even further preferably from 22 to 27° C., still further preferably at about 25° C. The ready-to-use application solution can be prepared by dispensing the liquid cleaning concentrate according to the invention. Optionally, the ready-to-use application solution can also be prepared manually starting from the liquid cleaning agent concentrate according to the invention.

The invention will now be described by way of example on the basis of certain advantageous embodiments with reference to the accompanying drawings. Shown are:

FIG. 1: Pressure-time graphs of a machine washing cycle with good pump pressure behavior (top) and poor pump pressure behavior (bottom)

Figure 2:
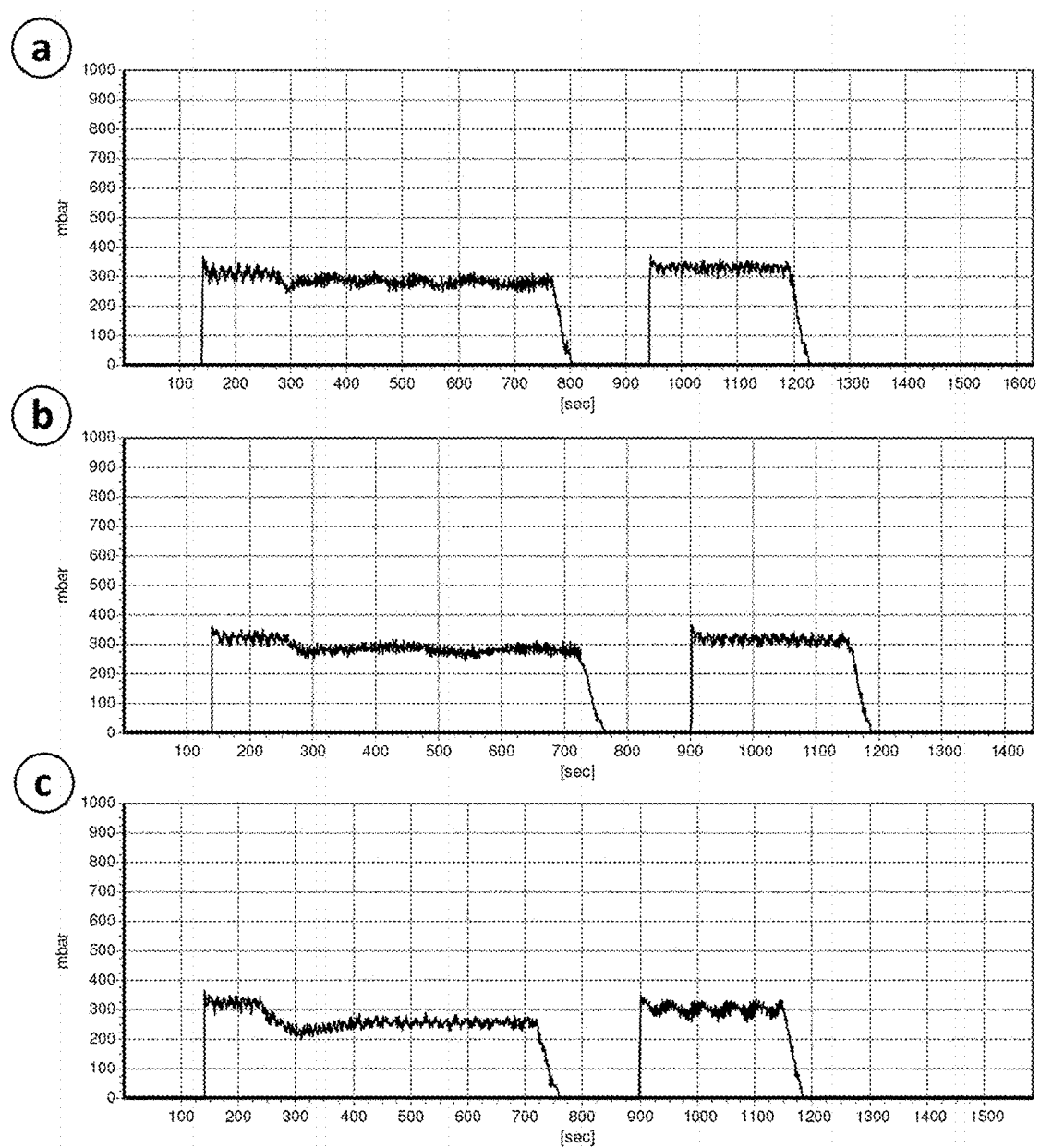
Figure 3:
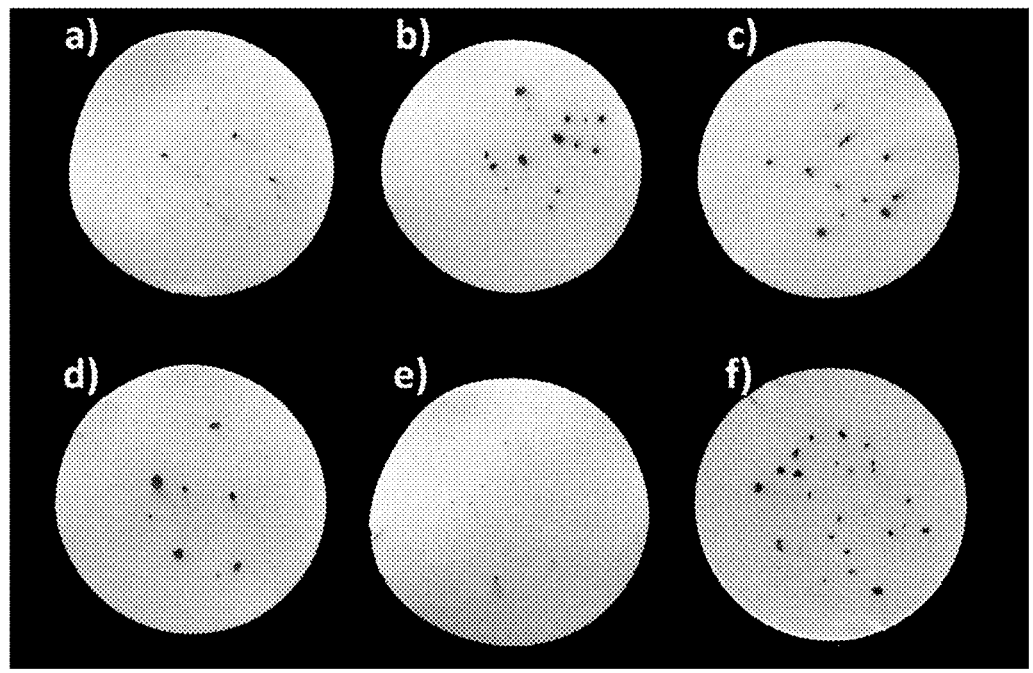
Figure 4:
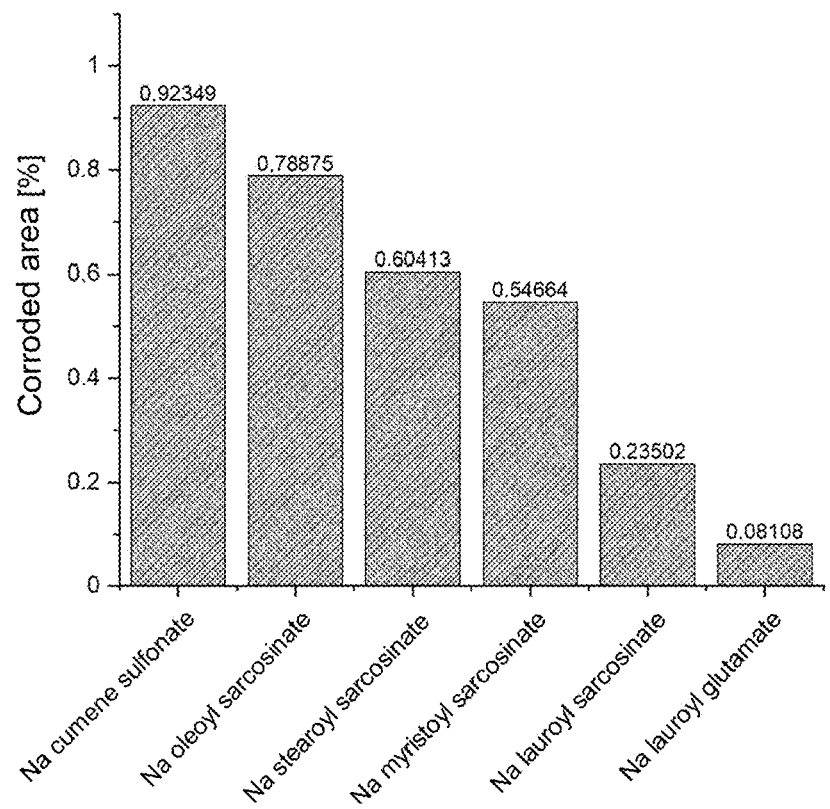

FIG. 2: Pressure-time graphs of a machine washing cycle with ready-to-use application solutions containing the fatty alcohol alkoxylates according to the invention, a) C12-C15 fatty alcohol radical having 2 EO/6 PO units, b) C12-C14 fatty alcohol radical having 2 EO/4 PO units and c) C12-C14 fatty alcohol radical having 4 EO/5 PO units FIG. 3: Corrosion behavior on GG25 gray cast iron tested in accordance with DIN 51360 Part 2 with ready-to-use application solutions comprising a) sodium lauroyl sarcosinate, b) sodium oleoyl sarcosinate, c) sodium myristoyl sarcosinate, d) sodium stearoyl sarcosinate, e) sodium lauroyl glutamate as amino acid-based surfactants according to the invention and f) sodium cumene sulfonate as reference formulation FIG. 4: Bar chart with quantitative results for the extent of corrosion with GG25 gray cast iron chips FIG. 5: Quantitative determination of the blood residues after immersion tests with sheep's blood and a mixture of sheep's blood and Betaisodona tincture FIG. 6: Pressure and temperature curves for cold water dispensing of a liquid cleaning agent concentrate according to the invention at a concentration of 3 ml/l at 25° C.

Figure 7:
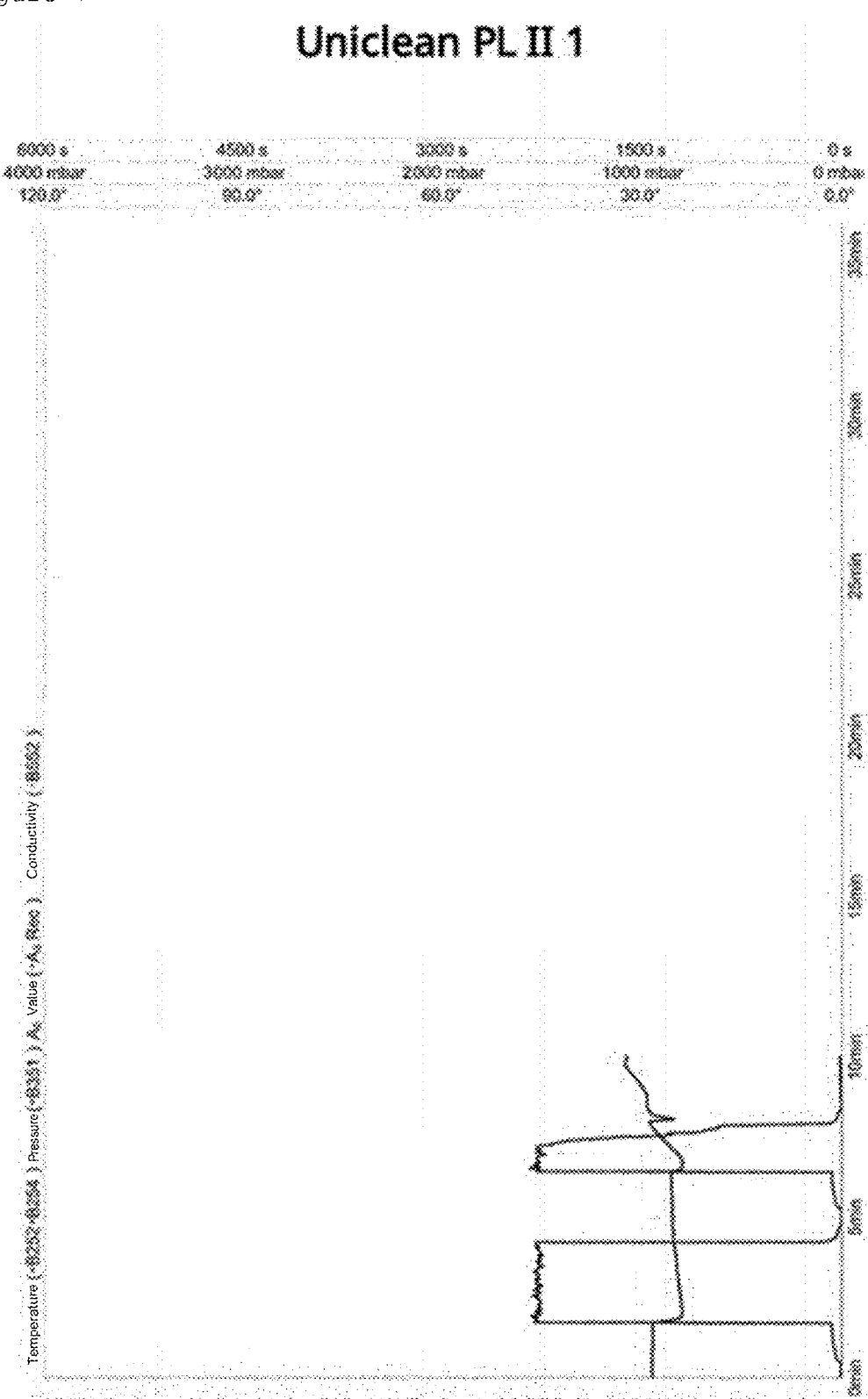

FIG. 7: Pressure and temperature curves for cold water dispensing of the commercially available cleaning agents known from the prior art at the respective standard recommended concentration at 25° C.

1. FATTY ALCOHOL ALKOXYLATE

Seven different fatty alcohol alkoxylates having variable chain lengths of the fatty alcohol radical and different degrees of ethoxylation or propoxylation (i.e. FA C12-C15 having 2 EO/6 PO, FA C12-C14 having 2 EO/4 PO, FA C12-C14 having 4 EO/5 PO, FA C12-C15 having 8 EO/4 PO, butyl-etherified FA C12-C14 having 10 EO, FA C12-C12 having 6 EO/8 PO, methyl-etherified FA C13-C15 having 5 EO/3 PO) were tested with regard to their foam-dampening properties in a ready-to-use application solution having an otherwise unchanged cleaning formulation. The respective suitability of the fatty alcohol alkoxylate for use in a machine cleaning process was assessed by measuring the metering pump pressure throughout a cleaning operation (cf. FIG. 1).

FIG. 1 shows a comparison of pressure-time graphs of a machine washing cycle with very good pump pressure behavior (top) and poor pump pressure behavior (bottom).

The fatty alcohol alkoxylates a) C12-C15 fatty alcohol radical having 2 EO/6 PO units, b) C12-C14 fatty alcohol radical having 2 EO/4 PO units and c) C12-C14 fatty alcohol radical having 4 EO/5 PO units were found to be particularly advantageous. The associated pressure-time graphs of the fatty alcohol alkoxylates according to the invention of the respective machine washing cycle are shown in FIG. 2. The fatty alcohol alkoxylates all exhibit very good pump pressure behavior.

2. Amino Acid-Based Surfactant

Five different amino acid-based surfactants (i.e. sodium lauroyl sarcosinate, sodium oleoyl sarcosinate, sodium myristoyl sarcosinate, sodium stearoyl sarcosinate, sodium lauroyl glutamate) were tested with regard to their corrosion-inhibiting properties in a ready-to-use application solution having an otherwise unchanged cleaning formulation in comparison with a reference formulation containing a common non-amino acid-based surfactant (i.e. sodium cumene sulfonate). For the assessment, corrosion tests were carried out with GG25 gray cast iron chips in accordance with DIN 51360 Part 2.

1. Corrosion Tests with GG25 Gray Cast Iron Chips in Accordance with DIN 51360 Part 2 a. Equipment and Materials

Petri dishes, ø100 mm (glass or plastic)
filter paper, ø70 mm, 589 from Whatman, ash-free, medium-fast filtration
GG25 gray cast iron chips according to DIN 51360 Part 2 (Riegger Industriehandel, article 03-39)
demineralized water b. Procedure Using a spoon spatula, 2 g±0.1 g of the chips were weighed onto the filter paper placed in the Petri dish. The chips were distributed as centrally as possible over an area of ø40-50 mm. The chips and the filter paper were wetted evenly with 2 ml of the 2.5% ready-to-use application solution and the Petri dish was sealed with the lid. The samples prepared in this way were stored for 2 hours±10 minutes at room temperature (20-25° C.) without direct sunlight or drafts. The chips were removed and discarded. The filter paper was rinsed under running demineralized water and rinsed in acetone for 5-10 seconds. The filter paper was dried at room temperature (20-25° C.). The degree of corrosion was determined immediately after drying. Each test was carried out in duplicate.

c. Evaluation

For the evaluation, instead of a visual assessment, the area of the corrosion that occurred was related to the total area of the filter paper used. The integrals of the areas were determined using ImageJ software.

d. Result

All the test preparations of the ready-to-use application solutions containing an amino acid-based surfactant show significantly improved corrosion inhibition behavior compared to the reference formulation without an amino acid-based surfactant. The best results are achieved with the ready-to-use application solutions containing the amino acid-based surfactants sodium lauroyl sarcosinate and sodium lauroyl glutamate. The corrosion behavior on GG25 gray cast iron can be seen in FIG. 3. The extent of corrosion in the tests with gray cast iron chips was quantitatively determined by subsequent integration of the corroded areas (see FIG. 4).

3. Hydrotrope

Eight different compounds from different classes of substance, i.e. each selected from alkyl ether carboxylic acids, alkyl sulfates, alkyl sulfonates, aromatic sulfonates, alkyl glycosides, alkyl diglycosides and alkyl polyglycosides, were tested for their suitability as a hydrotrope in ready-to-use application solutions. The test parameters used for the assessment were the cloud point and the metering pump pressure during a machine washing operation.

Surprisingly, the combination of constituents that is according to the invention achieves a cloud point of >40° C. for the ready-to-use application solutions. This is particularly advantageous because this is generally also the application temperature or the storage temperature in the washer disinfector. Especially the application solutions comprising alkyl sulfates as a hydrotrope show very good results. By contrast, the cloud point without the combination according to the invention is only around 20° C.

4. Combination of Fatty Alcohol Alkoxylate, Amino Acid-Based Surfactant and Hydrotrope Various combinations of amino acid-based surfactants and hydrotropes with the best fatty alcohol alkoxylate from the section above were tested in ready-to-use application solutions.

In immersion bath tests, the formulation variants were tested for their cleaning performance with regard to sheep's blood and a mixture of blood and Betaisodona tincture. In machine washing tests, the metering pump pressure was followed over the course of a complete cleaning cycle as a measure of the foaming behavior. At the same time, 10 ml of blood were additionally added to the cleaning bath, which causes increased foam formation and can simulate the reprocessing of heavily soiled instruments.

1. Cleaning Tests in the Immersion Bath a. Equipment and Materials stainless steel plate (slightly roughened, area 1 cm×9 cm)
sheep's blood, heparinized, with 10 IU/ml of
protamine sulfate or protaminechloride: ACILA GmbH
Betaisodona (10% povidone iodine solution)
marker dots, ø8 mm, different colors
demineralized water b. Procedure Preparation of Test Plates—Heparinized, Reactivated Sheep's Blood:

The heparinized sheep's blood and the protamine sulfate/protamine chloride were stored in a climate cabinet at 6° C. until the test. For the preparation of the test soiling, the sheep's blood and the protamine sulfate/protamine chloride should have reached a temperature of 20° C. The grease-free stainless steel plates were clamped on a rack and should be aligned horizontally as straight as possible.

75 µl of protamine sulfate or protamine chloride were briefly mixed with 5 ml of heparinized sheep's blood on a magnetic stirrer in a 50 ml glass beaker. 100 µl of this solution were pipetted onto each plate and distributed evenly with an inoculation loop without contaminating the mounting holes and the lateral surfaces. Each batch was then incubated for 1 hour at room temperature in water vapor-saturated air (100% air humidity or RH). The rack of plates can be immersed in the demineralized water, but the plates must be stored above the water level. To set 100% RH, the bottom of an 8.5 liter plastic container was filled with at least 1 liter of demineralized water. The demineralized water must completely cover the bottom of the horizontally placed tray. The tray was covered with a lid at least 2 hours before the start (conditioning of the atmosphere). After 1 hour, the wet test specimens with the coagulated blood soiling were removed from the plastic tray and dried at room temperature.

The quality of the dry test plates was checked. Plates with air bubbles on the soiling or showing irregularities were excluded. A green marker dot was glued to each of the other plates. The test plates were stored in test tubes with screw caps at room temperature until use in the immersion test.

Preparation of Test Plates—Iodine Blood:

The defibrinated sheep's blood was stored in a climate cabinet at 6° C. until the test. For the preparation of the test soiling, the sheep's blood should have reached a temperature of 20° C. The grease-free stainless steel plates were clamped on a rack and should be aligned horizontally as straight as possible.

The defibrinated sheep's blood was briefly mixed in a 1:1 ratio with Betaisodona on a magnetic stirrer in a 50 ml glass beaker. 200 µl of this solution were pipetted onto each plate and distributed evenly with an inoculation loop without contaminating the mounting holes and the lateral surfaces. The test plates were dried at room temperature for about six hours, but at least until all plates are visually dry. The quality of the dry test plates was checked. Plates with air bubbles on the soiling or showing irregularities were excluded. An orange marker dot was glued to each of the other plates. The test plates were stored in test tubes with screw caps at room temperature until use in the immersion test.

Immersion Test Procedure:
  Concentration: 2 ml/l
  Water quality: demineralized water
  Temperature: 45° C.±1° C.
  Holding time: 4 and 10 min
  Stirring speed: 350 rev/min (IKA RCT classic stirrer)
  Initial charge: 1000 ml solution in a 1000 ml glass beaker
  Test plate: heparinized, reactivated sheep's blood iodine blood The soiled test plates were each individually immersed into the solution. Removal was followed by brief immersion in cold demineralized water. The plates were dried horizontally at room temperature. The visual evaluation was carried out with the dried plates. The test plates with the soiling by heparinized, reactivated sheep's blood were stained with a 0.1% amido black solution.

c. Evaluation

The evaluation was carried out visually with the dried plates. In addition, the evaluation was also carried out here using the integrals of the remaining blood residues in relation to the total area of the test specimen with the aid of ImageJ software.

d. Results

Table 1 below summarizes the test results. In addition to the constituents listed in Table 1, the liquid cleaning agent concentrates tested were also prepared from the following, otherwise unchanged constituents:

| | |
|---|---|
| 3.5% by weight | endoprotease |
| 8.0% by weight | 45% KOH |
| 16% by weight | 99% triethanolamine |
| 12.0% by weight | 40% MGDA, 3Na |
| 10% by weight | 50% PBTC |
| to 100% by weight | water |

TABLE 1

Test results in relation to pump pressure and cleaning performance.

| | Fatty alcohol | Amino acid-based | Hydrotrope | Pump pressure | Cleaning performance |
|---|---|---|---|---|---|
| 1 | 0.5 wt % FA C12/C14 2EO/6PO | 0.5 wt % 30% Na lauroyl sarcosinate | 0.8 wt % 42% Na octyl sulfate | very good | very good |
| 2 | 0.5 wt % FA C12/C14 2EO/6PO | 0.5 wt % 30% Na lauroyl sarcosinate | 1.6 wt % 42% Na ethylhexyl | good | very good |
| 3 | 0.5 wt % FA C12/C14 2EO/6PO | — | 1.7 wt % 42% Na octyl sulfate | very good | moderate |
| 4 | 0.5 wt % FA C12/C14 2EO/6PO | 0.8 wt % 30% Na lauroyl | — | very poor | very poor |
| 5 | 0.5 wt % FA C12/C14 2EO/6PO | — | 15 wt % 40% Na cumene sulfonate | very good | poor |

The liquid cleaning agent concentrate comprising a combination of fatty alcohol alkoxylate and amino acid-based surfactant without the addition of a hydrotrope (comparative test 4) shows the worst cleaning performance and the worst pump pressure behavior of the test series. The second worst cleaning result is achieved by the liquid cleaning agent concentrate containing sodium cumene sulfonate (comparative test 5), though very good pressure behavior is observed here. The liquid cleaning agent concentrate comprising fatty alcohol alkoxylate and the hydrotrope sodium octyl sulfate (comparative test 3) shows very good pump pressure behavior with only moderate cleaning performance. The addition of the amino acid-based surfactant which cleans poorly in sole combination with the fatty alcohol alkoxylate (comparative test 4) led to very good cleaning performance of the liquid cleaning agent concentrate with a good pump pressure curve in the machine test (test 2).

The liquid cleaning agent concentrates according to the invention with the combinations of fatty alcohol alkoxylate, amino acid-based surfactant and hydrotrope (tests 1 and 2) achieve the best cleaning performances compared with the respective individual components and the various combinations of two constituents (comparative tests 3 to 5). A synergistic effect of the combination of fatty alcohol alkoxylate, amino acid-based surfactant and hydrotrope that is according to the invention is observed with regard to the removal of blood residues. The cleaning performance of the triple combination in the tests carried out is always better than that of the sum of the individual components.

Figure 5:
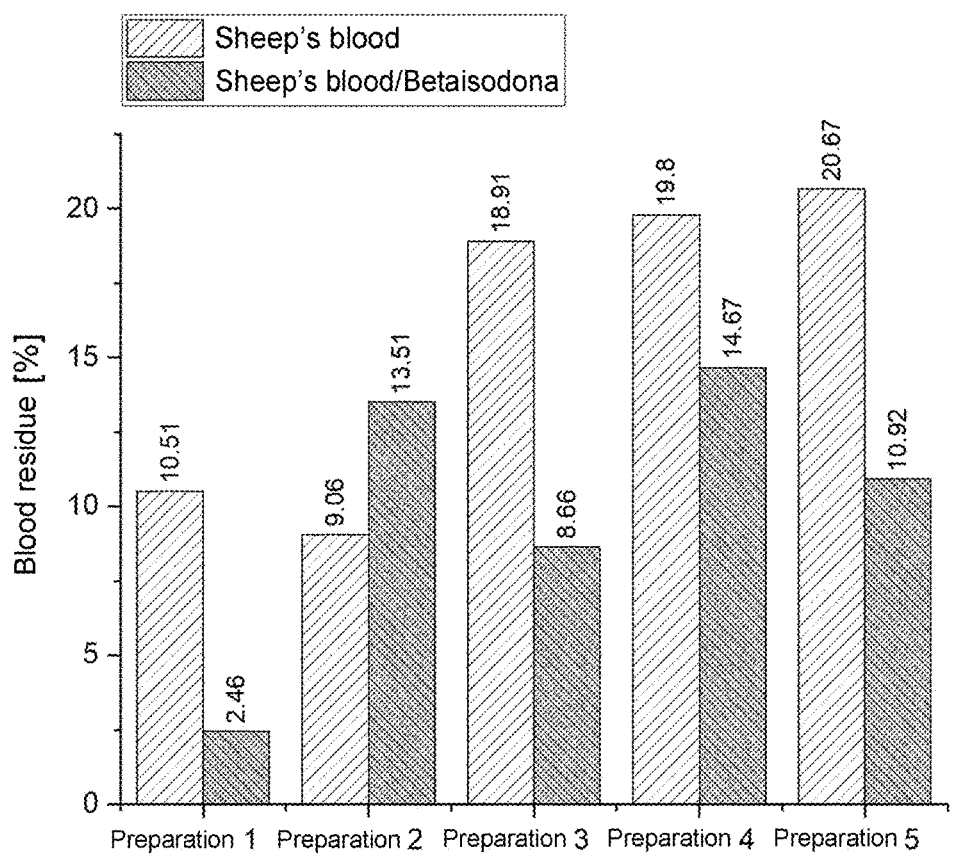

FIG. 5 shows a quantitative determination of the blood residues after carrying out the immersion tests with sheep's blood and a mixture of sheep's blood and Betaisodona tincture.

The results for preparations 1 to 5, listed in Table 1, are shown.

A further exemplary embodiment of a cleaning agent concentrate according to the invention that achieves approximately the same test results as the liquid cleaning agent concentrate from test example 1 consists of the following constituents:

| | |
|---|---|
| 0.5% by weight | FA C12/C15 2EO/6PO |
| 0.1% by weight | 96% cocoyl/lauroyl glutamate |
| 0.7% by weight | 42% Na octyl sulfate |
| 1% by weight | endoprotease |
| 14% by weight | 99% monoethanolamine |
| 6% by weight | amino carboxylate |
| 1% by weight | 75% phosphoric acid |
| to 100% by weight | water |

2. Cold Water Dispensing

In the prior art, the dispensing of surfactant-containing, enzymatic and mildly alkaline liquid cleaning agents for machine cleaning is usually done at a water temperature of about 40° C. This is necessary because the cleaning agents tend to foam excessively at lower temperatures. The disadvantage of dispensing at a temperature of about 40° C., however, is that the run time of the cleaning program is prolonged, since there is initially a certain time delay for heating up from the inlet temperature (usually ca. 18-22° C.) to a temperature of 40° C. before the cleaning agent can take effect.

The liquid cleaning agent concentrate and ready-to-use application solution according to the invention, in contrast, make it possible to carry out cold dispensing directly after the water inlet, preferably at a temperature of 38° C. or less, more preferably from 18 to 35° C., even more preferably from 20 to 30° C., still more preferably from 22 to 27° C., even further preferably at about 25° C., without the program being aborted due to excessive foam development. This is currently not possible with the cleaning agents known from the prior art.

Figure 6:
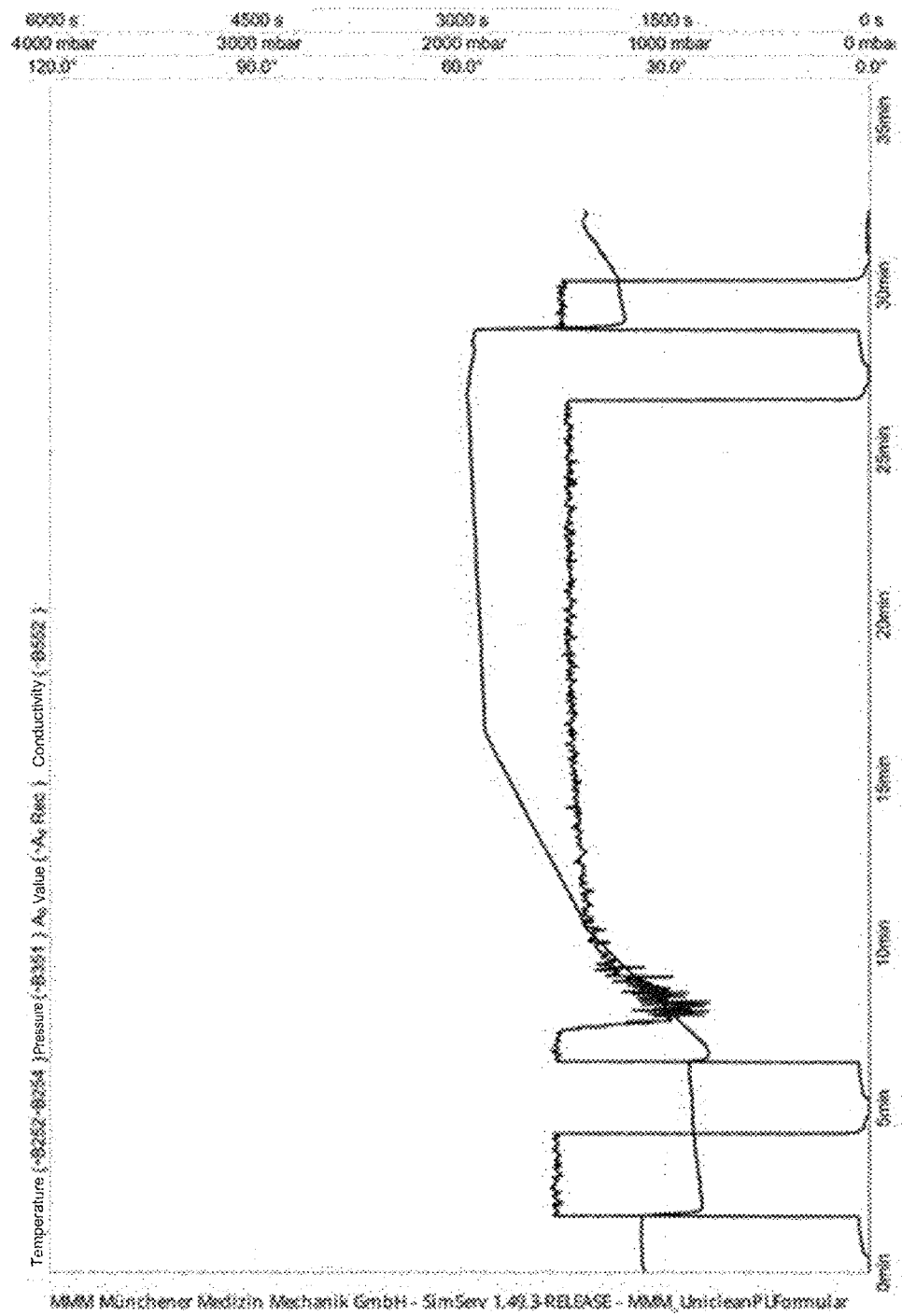

FIG. 6 shows the correct and complete program sequence (pressure and temperature curves) from a cleaning and disinfection system (UniClean PL II from MMM). Here, the liquid cleaning agent concentrate according to the invention was dispensed at a concentration of 3 ml/l at 25° C.

This was carried out analogously for several of the commercially available cleaning agents known from the prior art at the respective standard recommended concentration at 25° C. (including Dr. Weigert, neodisher Medi-Clean forte, 6 ml/l, #681964; Ruhof, Endozyme AW plus, 3.5 ml/l; Dr. Schumacher, thermoshield Xtreme, 3 ml/l, #460764; Borer, deconex Twin pH10 Twin Zyme, 3 ml/l+1.5 ml/l, #0370073+#0.397577; Prolystica, Prolystica 2× concentrate alkaline cleaner, 3 ml/l, #290186). For these cleaning agents, program termination is observed, as shown in FIG. 7.

The invention claimed is:

1. A liquid cleaning agent concentrate for machine cleaning and/or disinfection of medical and/or surgical instruments and/or apparatus, comprising:
   A) from 0.1 to 9% by weight of at least one fatty alcohol-based EO/PO copolymer;
   B) from 0.05 to 5% by weight of at least one amino acid-based surfactant having a saturated C10-C18 carbon radical;
   C) from 0.5 to 13% by weight of at least one hydrotrope selected from the group consisting of C6-C10-alkyl sulfates and sodium salts thereof, C6-C10-alkyl sulfonates, alkyl glycosides having a branched or unbranched C4-C16 alkyl radical, isooctylimino dipropionate, n-octylimino dipropionate, caprylic and capric amphopropionate; and
   D) from 0.05 to 4% by weight of at least one proteolytic enzyme, wherein the pH of the liquid cleaning agent concentrate is 9 or >9.

2. The liquid cleaning agent concentrate as claimed in claim 1, characterized in that the liquid cleaning agent concentrate has a pH of 9-12.

3. The liquid cleaning agent concentrate as claimed in claim 1, characterized in that the fatty alcohol-based EO/PO copolymer has at least one of the following features:
   comprises 1-4 EO units,
   comprises 1-8 PO units,
   has at least one C6-C16 fatty alcohol radical,
   is selected from the group consisting of C12-C15 fatty alcohol radical having 2 EO/6 PO units, C12-C15 fatty alcohol radical having 8 EO/4 PO units, butyl-or methyl-etherified C12-C14 fatty alcohol radical having 10 EO units, C10-C12 fatty alcohol radical having 6 EO/8 PO units, C12-C14 fatty alcohol radical having 2 EO/4 PO units, C12-C14 fatty alcohol radical having 4 EO/5 PO units, methyl-etherified C13-C15 fatty alcohol radical having 5 EO/3 PO units and C13-C15 fatty alcohol radical having 5 EO/3 PO units.

4. The liquid cleaning agent concentrate as claimed in claim 1, characterized in that the amino acid-based surfactant
   is selected from sarcosines, taurines, glutamic acids and salts thereof.

5. The liquid cleaning agent concentrate as claimed in claim 1, characterized in that the at least one hydrotrope is selected from:
   sodium octyl sulfate and sodium ethylhexyl sulfate;
   isooctylimino dipropionate, n-octylimino dipropionate;
   alkyl glycosides, wherein the glycoside radical is selected from hexose unit and pentose unit.

6. The liquid cleaning agent concentrate as claimed in claim 1, characterized in that the hydrotrope is sodium octyl sulfate, sodium ethylhexyl sulfate or a mixture thereof.

7. The liquid cleaning agent concentrate as claimed in claim 1, characterized in that the liquid cleaning agent concentrate also comprises further constituents selected from alkanolamines, alkali metal hydroxides, chelating agents, solvents, corrosion inhibitors, fragrances and dyes.

8. The liquid cleaning agent concentrate as claimed in claim 7, characterized in that the alkali metal hydroxide is potassium hydroxide.

9. A ready-to-use application solution comprising 0.05 to 99.9% of the liquid cleaning agent concentrate as claimed in claim 1, wherein the pH of the ready-to-use application solution is 9 or >9.

10. The ready-to-use application solution as claimed in claim 9, characterized in that the liquid cleaning agent concentrate has a pH of 9-12.

11. A method for cleaning medical and/or surgical instruments and/or apparatus, characterized by the following steps:
   a) preparing a ready-to-use application solution as claimed in claim 9, b) cleaning the medical and/or surgical instruments and/or apparatus with the ready-to-use application solution.

12. The method as claim in claim 11, characterized that the ready-to-use application solution is prepared at a temperature of 38° C. or less.

13. The liquid cleaning agent concentrate as claimed in claim 2, characterized in that the liquid cleaning agent concentrate has a pH of 10-11.

14. The liquid cleaning agent concentrate as claimed in claim 3, characterized in that the fatty alcohol-based EO/PO copolymer is selected from C12-C15 fatty alcohol radical having 2 EO/6 PO units, C12-C14 fatty alcohol radical having 2 EO/4 PO units and C12-C14 fatty alcohol radical having 4 EO/5 PO units.

15. The liquid cleaning agent concentrate as claimed in claim 4, characterized in that the amino acid-based surfactant is selected from lauroyl sarcosine and lauroyl glutamic acid and sodium salts thereof.

16. The liquid cleaning agent concentrate as claimed in claim 1, characterized in that at least one of the following constituents in the liquid cleaning agent concentrate is present at the following proportions by weight:

the fatty alcohol-based EO/PO copolymer at a proportion by weight of 0.4 to 2% by weight, based on the total mass of the liquid cleaning agent concentrate;

the amino acid-based surfactant at a proportion by weight of 0.1 to 2% by weight, based on the total mass of the liquid cleaning agent concentrate;

the hydrotrope at a proportion by weight of 0.15 to 3.5% by weight, based on the total mass of the liquid cleaning agent concentrate;

the proteolytic enzyme at a proportion by weight of 0.1 to 2% by weight, based on the total mass of the liquid cleaning agent concentrate.

17. The ready-to-use application solution as claimed in claim 10, characterized in that the liquid cleaning agent concentrate has a pH of 10-11.

18. The liquid cleaning agent concentrate as claimed in claim 1, characterized in that the amino acid-based surfactant is selected from lauroyl sarcosine, myristoyl sarcosine, stearoyl sarcosine, and lauroyl glutamic acid, and salts thereof.

* * * * *